United States Patent [19]

Nychka et al.

[11] 4,052,470

[45] Oct. 4, 1977

[54] PROCESS FOR THE PRODUCTION OF CHLOROFLUORINATED ACYCLIC HYDROCARBONS

[75] Inventors: Henry R. Nychka, East Aurora; Richard E. Eibeck, Orchard Park, both of N.Y.; Morris B. Berenbaum, Summit, N.J.

[73] Assignee: Allied Chemical Corporation, Morris Township, N.J.

[21] Appl. No.: 642,874

[22] Filed: Dec. 22, 1975

[51] Int. Cl.$^2$ .............................................. C07C 19/08
[52] U.S. Cl. ............................... 260/653.7; 260/653.6; 260/653.8
[58] Field of Search ................ 260/653.6, 653.7, 653.8

[56] References Cited

U.S. PATENT DOCUMENTS

| 2,578,913 | 12/1951 | Whitman | 260/653.8 |
| 3,398,203 | 8/1968 | Olson | 260/653.7 |
| 3,476,817 | 11/1969 | Vecchio | 260/653.7 |

FOREIGN PATENT DOCUMENTS

| 745,818 | 3/1956 | United Kingdom | 260/653.7 |

*Primary Examiner*—C. Davis
*Attorney, Agent, or Firm*—Jay P. Friedenson

[57] ABSTRACT

Chlorofluorinated acyclic hydrocarbons may be produced produced by a commercially viable oxychlorofluorination process by reacting a gaseous mixture of a starting material selected from an acyclic hydrocarbon containing up to four carbon atoms and an acyclic hydrohalocarbon containing up to four carbon atoms in which the halo atoms are selected from chloro and fluoro, or mixtures thereof, an oxygen-containing gas, a chlorinating agent selected from the group consisting of HCl and $Cl_2$ and mixtures thereof, and HF, in the presence of a Deacon catalyst supported by a stable, inert metal salt carrier.

74 Claims, No Drawings

PROCESS FOR THE PRODUCTION OF CHLOROFLUORINATED ACYCLIC HYDROCARBONS

BACKGROUND OF THE INVENTION

A standard commercial process for the production of chlorofluorinated acyclic hydrocarbons involves the reaction of carbon tetrachloride with hydrogen fluoride in the presence of a fluorination catalyst. In such process for each mole of hydrogen fluoride reacted there is one mole of hydrogen chloride liberated.

Because this by-product hydrogen chloride does not have a steady market even after purification from small amounts of hydrogen fluoride contaminant, it is usually disposed of by dumping in rivers or in the ocean where permitted. The extra cost of this type of disposal is borne by the manufacturing operation. Furthermore, in view of environmental considerations, it is probable that such disposals will be restricted or eventually banned.

Recently, a new process has been developed for the production of chlorofluorinated acyclic hydrocarbons which comprises reacting a mixture of an acyclic hydrocarbon and chlorine and hydrogen fluoride over a fluorination catalyst with a relatively large excess of recycled material consisting of underchlorinated and underfluorinated hydrocarbons. This process, which combines chlorination and fluorination in one step, however, produces more hydrogen chloride per unit weight of chlorofluorinated hydrocarbon than the standard commercial process referred to above. It thus intensifies rather than alleviates the hydrogen chloride by-product problem.

In view of the above discussion, it is apparent that there is a need in the industry for new technology for the manufacture of chlorofluorinated acyclic hydrocarbons which does not suffer from the hydrogen chloride by-product problem.

The oxychlorination of acyclic hydrocarbons by a Deacon type reaction is well known in the art. This involves the chlorination of an alkane or a chloroalkane with chlorine or hydrogen chloride in the presence of an oxygen-containing gas such as air, and in the presence of a Deacon-type catalyst such as a metal halide impregnated on a suitably carrier. It is postulated that in such an oxychlorination reaction, hydrogen chloride is oxidized to chlorine and water and the chlorine thus produced then reacts with the organic material. In this manner, by-product hydrogen chloride is eliminated or at least substantially minimized.

Vapor phase fluorination of chlorinated acyclic hydrocarbons with and without the presence of a catalyst is also well known.

The combination of an oxychlorination reaction and a fluorination or chlorofluorination reaction into a simultaneous one-step oxychlorofluorination process is suggested in British Pat. No. 745,818, published Mar. 7, 1956. Such a one-step process, if commercially feasible, would be of substantial value not only in the avoidance of the HCl problem but also in the potential savings in capital equipment and energy expenditure in the manufacture of chlorofluorinated acyclic hydrocarbons.

Unfortunately, the process as described in the British patent is not commercially practical. Our attempts to duplicate the catalyst systems described in the British patent were unsuccessful. The $CuCl_2$ loading recommended in the patent exceeded the absorptive capacity of the carrier by more than two-fold. The excess $CuCl_2$ loading was found to create serious operating problems such as plugging, corrosion and erratic performance because of undue vaporization and run-off of the $CuCl_2$. Another disadvantage found for such high $CuCl_2$ loading was that it deactivates the fluorination sites on the carrier thus causing a significant decrease in HF conversions.

Others have experimented with fluorination systems for hydrocarbons containing HF, HCl, oxygen and a Deacon type catalyst, but no one to date has reported a commercially feasible system capable of supporting on efficient oxychlorofluorination reaction. For example, U.S. Pat. No. 3,476,817, issued Nov. 4, 1969, discloses a chlorofluorination reaction in which a hydrocarbon is reacted with chlorine in the presence of HF, a Deacon type catalyst, and oxygen in an amount sufficient to improve the catalyst life. However, the oxygen according to this disclosure is not present in an amount sufficient to accomplish an effective Deacon reaction and accordingly an efficient oxychlorofluorination reaction does not take place. U.S. Pat. No. 2,578,913, issued Dec. 18, 1951, discloses the preparation of fluorinated hydrocarbons by reacting a hydrocarbon with HF, in the presence of oxygen, a Deacon-type catalyst and a hydrogen halide promoter, such as HCl. However, the hydrogen halide promoter according to the disclosure is not present in an amount sufficient to accomplish efficient chlorination and accordingly an efficient oxychlorofluorination reaction does not take place.

Accordingly, despite the potential advantages of an oxychlorofluorination process, such a process has not been commercialized. To the best of our knowledge, since publication of British Pat. No. 745,818, no attempts have been reported in the literature to make this a viable process. The reasons for this lack of interest and suspicion of impracticability of the oxychlorofluorination approach are many-fold. As mentioned above, the process as described in British Pat. No. 745,818 cannot be duplicated and cannot be readily adapted for commercially practical results. Further, persons skilled in this art would, in considering commercial feasibility of an oxychlorofluorination process, fear the possibility of explosion and the flammability of hydrocarbons in the oxygen-rich environment present. Also, the likelihood of hydrolysis of the products and/or underchlorinated and underfluorinated hydrocarbon intermediates is imminent since the reactions occur at relatively high temperatures in the presence of water. Another concern would be the possibility of substantial losses of starting materials, underchlorinated and underfluorinated hydrocarbon intermediates and products to combustion. Finally, it would be expected that the system would be unduly corrosive to known materials of construction due to the combined corrosive action of water, HCl and HF at the elevated temperatures required for the reaction.

GENERAL DESCRIPTION OF THE INVENTION

We have now discovered, contrary to the evidence in the prior art and the expectations of those skilled in this art, that an efficient, commercially feasible oxychlorofluorination process for the production of chlorofluorinated acyclic hydrocarbons can be achieved, provided that certain critically defined conditions are observed and that a critically defined catalyst system is employed. Contrary to expectation, if such conditions are met, the reaction can be readily controlled without undue danger from explosion and flammability, good yields of products can be obtained without undue loss due to hydrolysis or combustion reactions and, quite surprisingly, known materials of construction can be used for the apparatus with tolerable corrosion rates.

We have been able to accomplish this by reacting a gaseous mixture of a starting material selected from an acyclic hydrocarbon containing up to four carbon atoms and an acyclic hydrohalocarbon containing up to four carbon atoms in which the halo atoms are selected from chloro and fluoro, or mixtures thereof, at least .25 mole oxygen in an oxygen-containing gas for each C-H bond in the starting material, at least .50 mole HCl or equivalent amount of $Cl_2$ for each C-H bond and C = C bond present in the starting material and HF, in the presence of a Deacon catalyst supported by a stable inert metal salt carrier, with the weight percentage of cation in the Deacon catalyst ranging from about 0.6–20 based on the total cation content of the Deacon catalyst and metal salt carrier, at elevated temperature and with a contact time of from about 0.1 to 20 seconds. Successful results depend on the combination of use of the Deacon catalyst, with the cation content in the indicated weight percent range, use of the relatively short contact times specified, and use of the critically defined minimum oxygen and HCl or $Cl_2$ levels.

DETAILED DESCRIPTION OF THE INVENTION

We theorize that in the oxychlorofluorination reaction, chlorination, oxidation and fluorination reactions all take place simultaneously. The chlorination reaction replaces one or more available hydrogen atoms in the starting material with chlorine to give a chlorinated product and HCl. In the presence of a suitable Deacon catalyst, as will be described in more detail hereafter, the HCl is oxidized back to chlorine which then is available for further chlorination. Water is also formed. In the presence of a fluorination catalyst, or under suitable thermal conditions, the chlorinated products are fluorinated by HF to yield fluorinated products. It is not feasible to produce very highly fluorinated products in the oxychlorofluorination environment. Depending on the conditions chosen, the final products are more or less partially fluorinated and may or may not contain hydrogen.

The acyclic hydrocarbon starting materials for the oxychlorofluorination reaction may be saturated or ethylenically unsaturated materials of up to four carbon atoms. Such class of materials includes such compounds as methane, ethane, propane, butane, ethylene, propylene, butylene, isobutylene and butadiene. The preferred saturated acyclic hydrocarbons are methane and ethane. The preferred unsaturated acyclic hydrocarbons are ethylene and isobutylene. When unsaturated starting materials are employed, the reaction proceeds by addition of $Cl_2$ across the double bonds to saturate such bonds followed subsequently by substitution of one or more chlorine atoms with fluorine.

The acyclic hydrohalocarbon class of starting materials containing up to four carbon atoms in which the halo atoms are selected from fluorine and chlorine may also be saturated or ethylenically unsaturated. These materials must contain at least one hydrogen atom. The halo atoms may be all chloro, all fluoro, or both. Preferably, these starting materials contain more atoms of hydrogen than halogen. Still preferably, the number of fluorine atoms in the molecules does not exceed more than one for each carbon atom present. Illustrative suitable starting materials of this class are methyl chloride, methyl fluoride, monochlorodifluoromethane, methylene chloride, methylene fluoride, chloroform, ethyl chloride, ethylene chloride, ethylene fluoride, ethylene dichloride, ethylene difluoride, trichloroethane, vinylidene chloride, vinyl chloride, trichloroethylene, and the monochloro-, dichloro- and trichloro- propanes, butanes, butylenes and butadienes. The preferred aliphatic hydrocarbon starting materials are methyl chloride and ethyl chloride.

The "oxygen-containing gas" refers to oxygen or an oxygen-containing mixture with gases which are not reactive under the process conditions employed. Examples of suitable oxygen-containing gas mixtures include oxygen enriched air, air mixed with inert gases and mixtures of oxygen, air and inert gases. The theoretical quantity of oxygen in an oxygen-containing gas required for the oxychlorination reaction is the stoichiometric amount required to convert C-H bonds to C-Cl bonds in accordance with the following formula:

$$C\text{-}H + HCl + \tfrac{1}{4} O_2 \rightarrow C\text{-}Cl + H_2O$$

In other words, .50 mole oxygen for each C-H bond in the starting material is theoretically required. A 50% deficiency may be employed with satisfactory results, or at least 0.25 mole oxygen for each C-H bond in the starting material. Generally, it is preferred to employ up to about a 50% excess, or 0.75 mole oxygen for each C-H bond in the starting material. Large excesses of oxygen will not deleteriously affect the reaction except for the possibility of creating a flammability problem.

HCl or chlorine may be used as the chlorine source for the oxychlorofluorination reaction. If HCl is used, it may be supplied from an outside source or, it may be prepared in situ, by the reaction of the HF feed with a chlorine-containing hydrohalocarbon starting material if present.

The quantity of HCl or $Cl_2$ used in the reaction should be the stoichiometric amount required for hydrogen replacement and/or saturation of ethylenically unsaturated bonds in the starting material. The theoretical amount required is 1 mole of HCl or equivalent amount of $Cl_2$ (.5 mole) for each C-H bond and C = C bond present in the starting material. A 50% deficiency of HCl or equivalent amount of $Cl_2$, or .50 mole HCl or equivalent amount of $Cl_2$, for each C-H bond and C = C bond present in the starting material, may be employed with good results, particularly if it is desired to favor the production of lower chlorinated products. Excess HCl or $Cl_2$ may be used to insure maximum conversions of the highly chlorinated products without deleterious effects. If it is desired to preserve some C-H bonds in the final product, a somewhat greater deficiency of HCl or chlorine should be employed, but in no event less than 2.0 moles of HCl or equivalent amount of $Cl_2$ for each mole of starting material.

In the case that HCl is charged, such would be converted to chlorine by the Deacon reaction and chlorine would then be the active chlorinating agent.

The quantity of HF to be employed is equal to at least one mole of hydrogen fluoride per mole of starting material for every fluorine atom desired in the end product which is to be achieved by the fluorination reaction. As mentioned above, it is not feasible in the oxychlorofluorination environment to produce highly fluorinated products. For example, it is not feasible to obtain any substantial quantity of methane derivatives containing more than two fluorine atoms, or any substantial amount of ethane derivatives containing more than three fluorine atoms. Large excesses of hydrogen fluoride may be used, however, without adversely affecting the reaction and may in fact the advantageous in assisting in control over reaction temperatures. In the case of methane starting material, for example, the preferred molar ratio of HF to methane is about 1-2.5:1.

The Deacon catalysts are the oxychlorination or Deacon-type reaction catalysts which are well known in the art. The most active catalysts of this type are the oxides and halides of multivalent metals having variable valence states. Illustrative of such metals are Cu, Sn, Ni, Rh, Fe, V, Mn, Co, Pb, Cd, Hg, Pb, Ce and Cr. The preferred metal is Cu. The preferred forms of these metals are the halides, especially the chlorides. Illustrative suitable Deacon catalysts are $CuCl_2$, $Cu_2O$, CuO, $FeCl_2$, $FeCl_3$, FeO, $Fe_2O_3$, $Cu_2Cl_2$, $Cr_2O_3$, $CrCl_3$, $MnCl_2$, $MnBr_2$, $MnO_2$, $SnCl_2$, $NiBr_2$, $RhCl_3$, $VCl_3$, $CoO_2$, $PdCl_2$, $Cd(NO_3)_2$, $HgBr_2$, $PbCl_2$ and $Ce(NO_3)_3$. The preferred Deacon catalyst is copper chloride. Mixtures of Deacon catalysts may be employed. Other metal salts such as alkali or alkaline earth metal chlorides may be combined with the Deacon Catalyst. These may serve to promote the Deacon reaction, promote the fluorination and chlorination reactions or inhibit combustion and hydrolysis reactions. Illustrative suitable metal salts of this type are the chlorides of Li, Na, K, Rb, La, Th, Ce, Ta and Cs. In order to achieve a significant amount of promotion, it is desirable to use at least .5 mole of the metal salt promoter per mole of Deacon catalyst. Large excesses of the metal salt promoter will not deleteriously affect the reaction. Generally, it is preferable to employ from about 1-2 moles of metal salt promoter per mole of Deacon catalyst and, still preferably, about 1 mole of metal salt promoter per mole of Deacon catalyst.

The Deacon catalyst is used in combination with a stable, inert metal salt carrier.

By "stable" is intended to mean that the carrier is dimensionally and physically stable in the sense that when used in a fixed bed reactor, no more than 20% by weight of the carrier crumbles or converts to a powder from its original granular or pelleted form after 500 hours of operation, or when used in a fluidized bed reactor, the carrier does not undergo erosion or agglomeration to the extent that the particle size distribution changes sufficiently to adversely affect the operation of the fluidized bed. Acceptable particle size distributions for fluidized bed reactions are set by standard engineering practice well known to persons skilled in the art. It is also a characteristic of being "stable" for the purpose of this description that the carrier is substantially non-volatile and non-melting at temperatures up to about 550° C.

By "inert" is intended to means that which is or becomes substantially non-reactive with the organic starting materials, HF, HCl if used or prepared in situ, $Cl_2$ and $O_2$. Some minor reaction with the aforementioned materials can be tolerated provided that such reaction does not adversely affect the oxychlorofluorination reaction or the catalyst life. Alumina ($Al_2O_3$) is not considered to be inert within this definition because it undergoes substantial reaction with HF under oxychlorofluorination conditions. An example of a permissible minor reaction is the formation of small amounts of fluorides and/or oxyfluorides which will not further react with the aforementioned materials. The term "inert" is not intended to exclude catalytically active materials provided such materials satisfy the other requirements for being inert as described above. For example, a material satisfying the requirements for the stable, inert, metal salt carrier as defined herein, may also function as a fluorination or Deacon catalyst, as defined herein. In the latter event, for the purposes herein, the expression Deacon catalyst supported by a stable, inert metal salt carrier can refer to a single substance. A preferred embodiment of the stable, inert, metal salt carrier are those carriers which are fluorination catalysts, such as $AlF_3$.

A variety of metal salts meet these criteria of being stable and inert including, for example, chlorides, fluorides, oxyhalides, or oxides and admixtures thereof of Al, Mg, Ca, Ba, V, Th, Sr, Co, Ni, Cd, Pb, Cr and Fe, or combinations thereof. Illustrative suitable metal salts are $AlF_3$, $MgF_2$, $CaF_2$, $BaF_2$, $V_2O_3$, $ThF_4$, $SrF_2$, $CoF_2$, $NiF_2$, $CdF_2$, PbO, $CrF_3$ and $Fe_2O_3$. The preferred anion for the metal salt carriers is fluoride. The preferred cation is aluminum and the preferred support material is $AlF_3$. Depending on the results desired, choice of the stable, inert metal salt support may have a substantial influence on the particular oxychlorofluorination reaction involved. As indicated above, the support may catalyze the fluorination reaction. It may also influence the degree of Deacon reaction obtained, the degree to which the HF reactant is utilized and the loss of acyclic hydrocarbon and acyclic halohydrocarbon starting materials to combustion and hydrolysis.

The metal salt used as the support may be prepared beforehand or formed in situ during the reaction. For example, the Deacon catalyst may be impregnated on alumina (aluminum oxide). Under oxychlorofluorination conditions, particularly exposure to HF at elevated temperatures, the surface of the alumina is converted to $AlF_3$. The process aspects of this invention employing such catalysts are considered to be part of the invention herein, although this is not a preferred mode of operation. Preferably, the support throughout the oxychlorofluorination reaction comprises at least about 80% by weight of the metal salt and, still preferably, at least about 90% by weight of the metal salt. German Pat. No. 2,114,457 discloses a number of chlorofluorination catalysts including $CuCl_2$ impregnated on a support such as aluminum oxide in which the catalyst loading is between about 1-10 weight percent metal based on the total weight of the catalyst salts and the support material. It is disclosed that during the chlorofluorination reaction the surface of the aluminum oxide is presumed to be converted to $AlF_3$. However, it is not believed possible to achieve at least 80% weight percent $AlF_3$ in this manner, principally since the normal chlorofluorination reaction temperatures are not high enough for optimum conversions of aluminum oxide to $AlF_3$. Accordingly, at least 80 weight percent $AlF_3$ supported Deacon mixtures are considered to be novel and unobvious and are claimed separately herein.

The preferred support material, $AlF_3$, may be prepared by fluorinating alumina with HF at elevated temperatures. The alumina starting material for the supports is commercially available. Either the commercially available alpha or gamma aluminas may be employed; however, it has been found that a superior carrier is formed by fluorination of gamma alumina. The aluminas may be readily fluorinated in their commercially available form as granules or pellets with anhydrous HF diluted with nitrogen at temperatures ranging from about 200°-650° C. It is preferred to conduct a substantial portion of the fluorination at the upper portion of this range, preferably at about 550°-650° C. Most preferred, in fact, is to maintain the temperature at about 650° C for the entire fluorination. At low fluorination temperatures a mixture of alpha and gamma forms of $AlF_3$ is obtained. At high fluorination temperatures the alpha form of $AlF_3$ is obtained. It has been found that the alpha form of $AlF_3$ is superior to the gamma form for oxychlorofluorination purposes. The gamma form of $AlF_3$ may also be prepared by the fluorination of $AlCl_3$ or the thermal decomposition of $(NH_4)_3AlF_6$. The alpha form may also be readily prepared by reacting $Al(OH)_3$ with HF.

It is essential according to the invention process that the weight percentage of cation in the Deacon catalyst during the oxychlorofluorination reaction be in the range of 0.6-20, preferably 1-16 and, still preferably, 2-8, based on the total cation content of the Deacon catalyst and the stable, inert metal salt carrier. For the purpose of determining the weight percentage of cation in the Deacon catalyst, the presence of cations in any additional metal salt promoters which are not themselves Deacon catalysts, shall be ignored. It is within the scope of this invention to charge a supported Deacon catalyst to the oxychlorofluorination reaction in which the cation content of the Deacon catalyst exceeds the maximum 20 weight percent level defined herein and subsequently during the course of the oxychlorofluorination reaction to permit the Deacon catalyst cation content to fall to within the claimed limits. Use of a concentration of Deacon catalyst substantially in excess of the above-described 20 weight percent limitation on cation concentration, however, results in an unstable catalyst with low activity and which creates corrosion problems. Such catalysts cannot be fluidized if desired and cannot be reused.

For example, in the oxychlorofluorination reaction disclosed in British Pat. No. 745,818, it is disclosed that 31 weight percent $CuCl_2$ be impregnated into $AlF_3$/NaCl. On the basis of cation content of the Deacon catalyst based on the total cation content of the Deacon catalyst and the support, this amounts to 38.6 weight percent. Our attempts to duplicate this catalyst failed. Such 31 weight percent $CuCl_2$ loading exceeded the absorptive capacity of the carrier by more than twofold. Only 23 weight percent $CuCl_2$ was able to be impregnated. When this 23 weight percent $CuCl_2$ was tested in an oxychlorofluorination reaction, there was considerable run-off of $CuCl_2$ so that only about a 14 weight percent $CuCl_2$ loading was actually achieved. This run-off and the vaporization of the excess $CuCl_2$ caused severe operating problems, such as plugging and erractic performance. The excess $CuCl_2$ also created a corrosion problem with the metallic reactor walls. A low catalytic activity was also noted with this catalyst and this was attributed to be caused by the deactivation of fluorination sites on the carrier by the excess $CuCl_2$, thus decreasing HF conversions.

Any conventional technique may be employed for placing the catalyst material on the metal salt carrier. The object is to accomplish the most uniform distribution of catalytic material on the carrier as is possible. By way of illustration the catalytic material may be sprayed upon the support particles in mixing devices, a solution containing the catalyst may be sprayed into a fluidized bed of the carrier particles or the carrier particles may be simply immersed in a solution containing the catalyst material followed by evaporation of the solution.

Reaction temperatures are elevated and may vary depending on the starting material chosen, the catalyst and other factors. Generally, reaction temperatures should be maintained between about 300°-600° C., preferably between about 300°-550° C. and, still preferably, between about 350°-500° C. If the reaction temperature is excessive in a particular environment, then the combustion of the hydrocarbons or halohydrocarbons or the hydrolysis of the halohydrocarbons may become excessive. If the reaction temperature is unduly low there will be a decline in the chlorination and fluorination reactions. The ideal reaction temperature for a particular oxychlorofluorination environment will depend on the starting materials chosen, the catalyst and other factors, as can readily be determined by those skilled in the art assisted by the considerations discussed above.

Contact time is critical. Contrary to the disclosure of British Pat. No. 745,818 which suggests a contact time of approximately 24 seconds, it is essential not to employ a contact time over about 20 seconds. If contact times substantially above 20 seconds are employed, substantial losses to combustion and to hydrolysis occur and the production capacity per unit volume of catalyst decreases. For example, with the preferred catalyst system of $CuCl_2$ on $AlF_3$, at approximately 24 seconds contact time, production of $CO_2$ is 4-5 times greater than at a contact time of approximately 2-6 seconds. If the contact times are too low, satisfactory conversion rates cannot be obtained. Accordingly, contact time must be maintained between about .1 to 20 seconds, preferably between about 2-12 seconds. For fixed bed operation, the preferred contact time is from about 1-18 seconds and, still preferably, from about 2-6 seconds. For dynamic or fluidized bed operation, the preferred contact time is between about 3-20 seconds and, still preferably, from about 6-12 seconds. By "contact" time (C.T.) is intended to means essentially the residence time that the feed materials contact each other in the presence of the catalyst, or, more precisely in the case of a fixed bed design (X):

$$C.T.X. \text{ (seconds)} = \frac{\text{Catalyst Volume (ml)} \times 273 \text{ ° K} \times 3600 \text{ sec/hr} \times \text{pressure (atm)}}{22,400 \text{ ml} \times \text{reactor temperature (° K)} \times \text{moles(reactants)/hr.}}$$

In the case of a fluid bed design (L):

$$C.T.L. \text{ (seconds)} = \frac{\text{Bed Height (ft.)}}{\text{Superficial Gas Velocity (ft./sec)}*}$$

Pressure is not a critical consideration as the reactions described herein may be conducted under atmospheric pressure or superatmospheric pressures. In the preferred embodiment, superatmospheric pressures are employed, preferably up to about 200 p.s.i.g. and, still preferably, from about 20-75 p.s.i.g.

The chlorination, fluorination and Deacon reactions are highly exothermic. It is desirable to control the exothermic heat of such reaction to avoid pyrolysis, carbonization, combustion and other undesirable side reactions.

* $\frac{\text{Volume of gas/sec. (ft.}^3\text{/sec)}}{\text{cross-sectional area (ft.}^2\text{) of reactor}}$ Mechanical cooling means may be employed to control the exotherm, such as cooling jackets, cooling spray, cooling coils or other suitable heat exchange means. Another way to control the exotherm is by diluting the catalyst with an inert, solid material such as fused alumina.

Another way to control the exotherm is by adding an inert gas to the reaction gas stream. By "inert gas" is intended to mean an organic or inorganic gas which is inert to reaction with the organic reactants and with chlorine, oxygen, water or HCl, but not necessarily inert to reaction with hydrogen fluoride. Illustrative suitable inert inorganic gas diluents are nitrogen, hydrogen chloride, helium and argon. Illustrative suitable inert organic gas diluents are $CCl_3F$, $CCl_2F_2$, $CClF_3$ and $CCl_4$.

The amount of diluent to be used is that which is needed to control the reaction temperature of the particular reaction involved. This will depend on the amount of chlorination taking place and the nature of the diluent used. The preferred amount of diluent may be readily determined by those skilled in the art. Generally, the molar ratio of the diluent to the carbon containing feed materials ranges from about 0.5–4:1, with the preferred ratio ranging from about 1–2:1. At the end of the reaction, the diluent may either be recycled or discarded.

The preferred way to control the exotherm is by recycling one or more halogenated hydrocarbons from the product mixture to the reaction mixture. The recycled halogenated hydrocarbons may be partially chlorinated reaction products, completely chlorinated reaction products and/or underfluorinated reaction products. The recycled halogenated hydrocarbons may be inert to further reaction or they may be subject to further reaction. In the case of methane, for example, the recycled halogenated hydrocarbon may be a single substance such as $CCl_4$ or $CFCl_3$, or a mixture of same and underchlorinated and other underfluorinated methanes. In the case of ethane, for example, the recycle can be a single compound such as $C_2Cl_4$ or $C_2Cl_3F_3$, or a mixture of the same with underchlorinated and other underfluorinated ethanes. If a recycle medium is employed, about 1–6:1 molar ratio of recycled halogenated hydrocarbon to hydrocarbon starting material should be employed, with a preferred molar ratio of about 2–4:1. There is nothing critical about the upper limit for the concentration of the recycled products, except from the standpoint of unit capacity and economy.

In addition to the advantage of providing control over reaction exotherm, use of a recycle affords the advantages of higher utilization of HF, attainment of higher yields of the more fluorinated products, a more efficient use of oxygen, less combustion, higher conversion of reactants and a means of control over final product distribution. A high HF utilization is particularly important since recovery of substantial amounts of unreacted HF for recycling is expensive and adds substantially to manufacturing costs. Recycle with underfluorinated products results in further fluorination of the underfluorinated recycle material and thus provides control over the desired product distribution in the final product mix.

Simple experimentation with the make-up and quantity of the recycle in a particular environment will permit ready determination of optimum HF utilization conditions and optimum conditions for achieving the product distribution desired.

Attainment of the above-described advantageous results with a recycle was surprising in the environment of this invention. The advantageous use of recycle in a chlorofluorination reaction is disclosed in U.S. Pat. No. 3,442,962. The environment of the present invention is significantly different from that of U.S. Pat. No. 3,442,962, however, in that the invention environment contains a significant amount of oxygen and water which is a by-product of the Deacon reaction. The literature would suggest that acyclic hydrocarbons and chlorinated acyclic hydrocarbons would be grossly decomposed by the oxidative and hydrolytic environment of this invention. (*Oxidation and Hydrolysis* of $CH_4$, Encyclopedia of Chemical Reactions, C. A. Jacobsen, Vol. II, Entries 1124, 1125, 1130, 1140, 1141, 1143, 1161; Oxidation and Hydrolysis of $CCl_4$, Organic Chlorine Compounds, E. H. Huntress, p. 578; *Oxidation and Hydrolysis* of $CHCl_3$, Organic Chlorine Compounds, E. H. Huntress, pp. 550–551.) Contrary to this expectation, under the conditions described herein, the loss of acyclic hydrocarbon starting materials, such as methane, and chlorinated acyclic hydrocarbons to combustion and hydrolysis is very minor.

Any combination of the above-described means of temperature control may be employed.

Th process of the invention is carried out by passing the gaseous reactants through a bed of the supported catalyst material in finely divided or granular solid form. The catalyst bed may be operated as a fixed bed, that is to say by keeping the gas velocity low enough that the bed of solid catalyst particles remains essentially static. The catalyst bed may also be operated as a dynamic bed. By increasing the gas velocity of the reactants some of the catalyst particles become dynamically suspended in the reactant gas stream. The height of the catalyst bed therefore expands. Such beds are generally referred to as "dynamic beds". As is known in the art, if the gas velocity is increased still further, all the catalyst bed particles become suspended and ultimately the bed may assume a highly turbulent condition known and referred to as a fluidized bed. Exact conditions required to establish a fluidized bed condition depend on the particle size of the catalyst components, the gas velocity, the density of the particles and other factors. A discussion of such factors as are necessary for establishing and maintaining a fluidized bed may be found in Wilhelm Kawak *Chemical Engineering Progress,* Vol. 44, Page 201 (1948).

Preferably the process of the invention is carried out in a continuous manner using a reactor comprising a plurality of vertical tubes which are charged with the supported catalytic material in finely divided or granular form. Preferably the catalyst is maintained in a fluidized state. The acyclic hydrocarbon starting material, the oxygen-containing gas, the chlorinating agent and hydrogen fluoride are metered into the bottom of the reactor tubes through the calibrated flowmeters. Prior to entry into the bottom of the reactor tubes the reactants are pre-heated to approximately the reaction temperature desired. Separate feed lines should be used for materials which would otherwise prematurely react before passage to the reactor tubes. For example, methane and chlorine will react thermally if present in the same heated lines, as will HF and $CCl_4$. Accordingly, these materials should be fed through separate lines. In accordance with the description herein, optional additional feed streams may be fed into the bottom of the reactor, such as a halogenated hydrocarbon recycle stream, and an inert diluent stream. Liquid reactants may be metered from calibrated reservoirs through pumps.

At the inlets to the fixed catalyst bed, relatively short hot zones will develop. These zones are generally 50°–100° C higher in temperature than the reactor temperatures. Such temperature gradients are tolerable, however, if excessive temperatures are generated in the hot zones, undesirable combustion and carbonization reactions could result. In such an event, the temperatures of such hot zones should be controlled by employing any of the methods discussed herein for exotherm control.

Pressures, temperatures, contact times and flow rates of reactants are regulated to produce the desired product composition with optimum yields and utilizations of reactants in accordance with the discussion herein. Reaction products are continuously removed from the top of the reactor tubes.

Recovery and purification of the desired products, by-products and unreacted reactants, may be accomplished by conventional means such as distillation procedures normally conducted at elevated pressures. For example, in the case of the oxychlorofluorination of methane, catalyst particles carried over in the exiting product gases may be separated by cyclones for return to the reactor. The product gases may then be cooled and partially condensed. Condensed aqueous HCl and HF are phase-separated from condensed organics, and may be recycled to the reactor after partial or complete dehydration. Condensed organics may be revaporized for further purification, or treated as a liquid phase. Organic vapors are neutralized by contacting with dilute caustic in a scrubber. The organic vapors may then be dried by contacting with concentrated sulfuric acid. The dried neutralized organic vapors are then compressed and fed to a distillation unit (still) to separate low boiling components, such as $CO_2$, oxygen, $CH_4$, $CClF_3$ and other trace low boilers, from higher boiling components such as $CCl_4$, $CCl_3F$, $CCl_2F_2$, $CHCl_3$, $CH_2Cl_2$ and other materials. A series of continuous distillations is used to separate the higher boiling materials into products, such as $CCl_3F$, $CCl_2F_2$, and chlorinated or partially chlorinated intermediates, such as $CCl_4$, $CHCl_3$, $CH_2Cl_2$, and other trace materials. The products may be further purified, if desired, by contacting with molecular sieves, or may be recycled to the reactor, depending on the product distribution desired.

A variety of modifications and variations of product recovery and purification may be employed by persons skilled in the art and will depend on the nature of the feed materials and product mixes obtained. Such procedures are well within the skill of the art and do not form a part of this invention.

Materials of construction for the reactor and associated equipment should be resistant to the reactants in the environment employed. In general, metals such as Inconel and Hastelloy are sufficiently resistant to corrosion in the presence of the reactants of the oxychlorofluorination process. The corrosion rate is lower in fluidized bed operations than in fixed bed operations. For this reason alone, fluid bed operation is preferred. In both fluid bed operation and fixed bed operation liners of fused high purity alumina (99.8%) perform well in terms of exhibiting low corrosion rates, withstanding high temperature exposure and providing good heat transfer through the reactor walls. Sintered Inconel 600 has proved of particular value as a construction material for the distributor bed supports in the fluid bed reactor.

The following examples illustrate practice of the preferred embodiment of the invention which is the oxychlorofluorination of methane and attempts to practice the invention described in British Pat. No. 745,818. The advantages of the present invention will be apparent therefrom. In the examples, the stated reactant feed rates were measured at 25° C./atmospheric pressure, temperatures refer to degrees Centigrade, and the following terms, unless otherwise specified, have the meanings given below. All quantities of materials referred to are in moles and all percentages given are on a weight basis, except for the terms defined below or unless otherwise specified.

$$\% \text{ HCl Conversion (moles)} = \frac{\text{HCl in} - \text{HCl out}}{\text{HCl in}} \times 100$$

$$\% \text{ HCl Utilization* (moles)} = \frac{\text{HCl in} + \text{HF consumed} - \text{Cl}^-\text{out}}{\text{HCl in} + \text{HF consumed}} \times 100$$

(*If $Cl_2$ is in feed, then substitute $Cl_2$ in for HCl in.)

$$\% \text{ Cl}_2 \text{ Utilization (moles)} = \frac{[(2 \times Cl_2 \text{ consumed}) + \text{HF consumed}] - \text{Cl}^-\text{out}}{(2 \times Cl_2 \text{ consumed}) + \text{HF consumed}} \times 100$$

$$\% \text{ Cl}_2 \text{ Conversion (moles)} = \frac{Cl_2 \text{ in} - Cl_2 \text{ out}}{Cl_2 \text{ in}} \times 100$$

$$\% \text{ HF Conversion (moles)} = \frac{\text{HF consumed}}{\text{HF in}} \times 100$$

$$\% \text{ HF Utilization (moles)} = \frac{\text{HF consumed} - \text{equivalent moles F in by product**}}{\text{HF consumed}} \times 100$$

(**$CF_3Cl$, $CHF_3$)

$$\% \text{ CH}_4 \text{ Conversion (moles)} = \left[ \frac{CH_4 \text{ in} - CH_4 \text{ out}}{CH_4 \text{ in}} \right] \times 100$$

$$\% \text{ CH}_4 \text{ Utilization (moles)} = \left[ \frac{(CH_4 \text{ in} - CH_4 \text{ out}) - (CO_2 + CClF_3 + CHF_3)}{CH_4 \text{ in} - CH_4 \text{ out}} \right] \times 100$$

-continued $$\% \text{ CH}_4 \text{ Yield (moles)} = \frac{\% \text{ CH}_4 \text{ Conversion} \times \% \text{ CH}_4 \text{ Utilization}}{100}$$

$$\% \text{ CO}_2/\text{CH}_4 \text{ (moles)} = \frac{\text{CO}_2 \text{ out}}{\text{CH}_4 \text{ in}} \times 100$$

$$\% \text{ O}_2 \text{ Conversion (moles)} = \left[\frac{\text{O}_2 \text{ in} - \text{O}_2 \text{ out}}{\text{O}_2 \text{ in}}\right] \times 100$$

$$\% \text{ O}_2 \text{ Utilization (moles)} = \left[\frac{(\text{O}_2 \text{ in} - \text{O}_2 \text{ out}) - \text{CO}_2}{\text{O}_2 \text{ in} - \text{O}_2 \text{ out}}\right] \times 100$$

$$\% \text{ O}_2 \text{ Yield (moles)} = \frac{\% \text{ O}_2 \text{ Conversion} \times \% \text{ O}_2 \text{ Utilization}}{100}$$

| | |
|---|---|
| ml | = Milliliters |
| g | = Grams |
| m²/g | = Square Meters/Gram |
| cc/g | = Cubic Centimeters/Gram |
| l/h | = Liters/Hour |
| I.D. | = Internal Diameter |
| m/h | = Moles/Hour |

EXAMPLE 1

This example demonstrates a typical preparation of AlF₃, the preferred carrier material:

A 834 g. sample of 1/8 inches diameter alumina pellets (Harshaw Al-1404), having a surface area of 190 m²/g and a pore volume of 0.46 cc/g, was charged to a 2 I.D. × 22 inches long Inconel tubular reactor to form a bed. The reactor was immersed in a fluidized sand bath the temperature of which was controlled at 550°±5°. During the heating up period, 25 g. of water were evolved under a small nitrogen sweep of 5 l/h. A stream of HF varying between 50–57 g/h and diluted with N₂ was then introduced. A "hot spot" temperature ranging from 644° to 662° immediately developed and gradually migrated from the inlet end of the bed to the outlet end. The signs of the completion of fluorination were: (1) HF was no longer being absorbed as measured by comparing HF input against HF output and (2) the "hot spot" temperature decreased to the level of the sand bath temperature of 550°. After 20 hours the fluorination was complete but HF introduction was continued for three hours more. The AlF₃ content in the resulting catalyst pellets was 90%. The catalyst had a pore volume of .13 cc/g and a surface area of 3.4 m²/g. X-ray diffraction pattern indicated the alpha form of AlF₃.

EXAMPLE 2

This example demonstrates impregnation of the AlF₃ carrier material prepared according to Example 1, with the preferred Deacon catalyst, CuCl₂. The catalyst was promoted with KCl.

125 ml of an aqueous solution of CuCl₂·2H₂O (16.0 g.) and KCl (7.0 g.) were added to the AlF₃ prepared according to Example 1, which was contained in a flask under vacuum. The flask contents were shaken slightly to insure a uniform coating of the pellets. After drying overnight at 100° in vacuo, the AlF₃ contained 2.0% CuCl₂ and 1.1% KCl or, on a metal basis, 95.3% Al, 2.9% Cu and 1.8% K.

EXAMPLE 3

This example shows a typical oxychlorofluorination procedure carried out according to the preferred methane embodiment of the invention:

A 450 ml or 591 g. sample of the supported catalyst prepared according to Example 2 and preconditioned by heating to 400° – 500° for two hours with HF at a flow rate of 40 g/h was charged into a 1¼ I.D. × 22 inch long Inconel pipe reactor to a depth of 14 inches. The reactor was immersed into a temperature controlled sand bath at 400° C. With the sand bath temperature at 400°, flow of CH₄, Cl₂, HF and CCl₄, at the rates indicated below, was started through the reactor. CCl₄ was used to simulate a recycle gas. Fifteen minutes later flow of O₂ was started. To obtain a 10 second contact time for a 450 ml. of catalyst at 400° the following flow rates were used. The corresponding molar ratios are shown.

| | Flow Rate (m/h) | Molar Ratio |
|---|---|---|
| CH₄ | 0.44 | 1.00 |
| Cl₂ | 0.55 | 1.25 |
| HF | 0.65 | 1.48 |
| O₂ | 0.61 | 1.38 |
| CCl₄ | 0.62 | 1.40 |

The stoichiometry for the reaction is as follows:

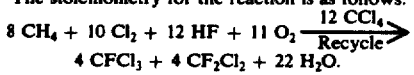

$$8 \text{ CH}_4 + 10 \text{ Cl}_2 + 12 \text{ HF} + 11 \text{ O}_2 \xrightarrow{12 \text{ CCl}_4 \text{ Recycle}}$$
$$4 \text{ CFCl}_3 + 4 \text{ CF}_2\text{Cl}_2 + 22 \text{ H}_2\text{O}.$$

All gas flows were measured by calibrated flowmeters. HF flow was measured by a differential pressure cell and the liquid flow was measured with a calibrated pump. After about one hour the temperature profile of the catalyst had stabilized. The "hot spot" temperature was 518° and was located at the inlet to the bed. It decreased abruptly as the distance from the inlet end increased as shown by the following temperature profile data.

| Distance from Inlet (Inches) | Temperature (°) |
|---|---|
| 0 | 518 |
| 2 | 469 |
| 4 | 421 |
| 6 | 409 |
| 8 | 406 |
| 10 | 406 |
| 12 | 403 |
| 14 | 394 |

Sand Bath Temperature 400°.

The reaction was conducted over a 5.5 hour period under the above specified conditions during which time effluent samples were taken at various intervals for wet and gas chromatographic (GC) analyses. The GC analysis was conducted by a direct on-line injection method. Prior to the analyses, the acidic components of the effluent samples were removed by condensation and phase separation. The results of the analyses after one hour of reaction were typical of those obtained over the entire 5.5 hour reaction period and are as follows:

| GC ANALYSIS | | | |
|---|---|---|---|
| Component | Wt. % | Component | Wt. % |
| $O_2$ | 2.0 | Unknown | 0.2 |
| CO | 0.1 | $CHCl_2F$ | 0.8 |
| $CO_2$ | 3.2 | $CCl_3F$ | 41.4 |
| $CH_4$ | 0.2 | $CH_2Cl_2$ | 2.8 |
| $CCl_2F_2$ | 2.8 | $CHCl_3$ | 11.0 |
| | | $CCl_4$ | 35.0 |
| | | Unknown | trace |

WET ANALYSIS
(Analysis of the Effluent for $Cl^-$, $F^-$ and $CO_3=$)
HF Conversion — 94 %
HCl Utilization — 62 %
Extent Combustion
(expressed as $\frac{CO_2 \text{ (moles)}}{CH_4 \text{ (moles)}} \times 100$) — 25 mole %

$Cl_2$ Conversion (in/out basis) - about 99 %
$CH_4$ Conversion — about 95-99 %

The $CO_2/CH_4$ value is an indication of the yields of chlorinated and chlorofluorinated products versus the amounts of the methane starting material lost to combustion and other oxidation reactions as indicated by $CO_2$ formation. The 25% figure indicates that 25 mole percent of the methane starting material was lost to $CO_2$ by combustion, with the balance of 75 mole percent being converted to chlorinated and chlorofluorinated products.

The high HF conversion indicates that good yields of chlorofluorinated products were obtained.

EXAMPLES 4–12

These examples were conducted identically to Example 3 except that the catalyst composition varied as indicated in the following Table. For ease of reference, the results obtained with the catalyst composition of EXAMPLE 3, are also shown:

EXAMPLE 13

This Example demonstrates an oxychlorofluorination reaction in which the chlorine is generated in situ by the reaction of HF with a chlorine-containing hydrohalocarbon starting material. A 620 ml (629 g.) sample of granular $Cr_2O_3$ was impregnated with 7.8% $CuCl_2/3.5\%$ KCl to give a catalyst having a metal composition of 90.6% Cr, 6.3% Cu and 3.1% K (Deacon cation concentration — 6.5%). An HF stream at the rate of 50 g/h was passed through the impregnated material for 8 hours at a temperature ranging from 340° to 410° to form $CrF_3$. On the basis of weight gain, the $CrF_3$ content of the catalyst was about 42%.

A gaseous mixture of $CHCl_3$, HF and $O_2$ in a mole ratio of 1.0/3.8/0.37 was passed through the thus prepared $CrF_3$ catalyst at 400° and with a contact time of about 13.6 seconds. After about one hour, wet analysis of the effluent after removal of the acidic components by condensation and phase separation, showed an HF conversion of 67% and an HCl utilization of 34%. GC analysis of the organic portion of the same effluent showed the following:

| Component | Wt. % | Component | Wt. % |
|---|---|---|---|
| $CCl_4$ | 0.7 | $CHCl_3$ | 0.2 |
| $CFCl_3$ | 16.8 | $CHFCl_2$ | 1.5 |
| $CF_2Cl_2$ | 44.4 | $CHF_2Cl$ | 3.7 |
| $CF_3Cl$ | 8.0 | $CHF_3$ | 24.5 |

The above data demonstrate that the oxychlorofluorination reaction proceeded efficiently.

EXAMPLE 14

A 450 ml sample of ¼ inch diameter $BaSO_4$ pellets was impregnated with 6.0% $CuCl_2$ and 1.7% KCl to give a catalyst having a metal composition of 93.6% Ba, 4.8% Cu and 1.6% K (Deacon cation concentration - 4.9%). A gaseous mixture of $CH_4/Cl_2/HF/O_2/CCl_4$ in the mole ration of 1/1/1.5/1.38/1.5 was passed through a bed of the catalyst at 350°. The contact time was 10.8 seconds.

Wet analysis of the effluent after removal of the acidic components by condensation and phase separation, showed the following:

TABLE I

| EXAMPLE | % Al | Cu | K | OTHER METALS | | CATION CONTENT OF DEACON CATALYST** | % HF CONVERSION | % HCl UTILIZATION | % $Cl_2$ UTILIZATION | % $CO_2$ /$CH_2$ | % $Cl_2$ CONVERSION |
|---|---|---|---|---|---|---|---|---|---|---|---|
| 3 | 95.3 | 2.9 | 1.8 | | | 3.0 | 94 | 62 | 74 | 25 | >99 |
| 4 | 74.3 | 16.0 | 9.7 | | | 17.8 | 68 | 74 | 81 | 9 | 85 |
| 5 | 99.1 | .60 | .34 | | | .60 | 91 | 38 | 59 | 9 | 98 |
| 6 | 78.2 | 8.0 | 4.9 | La | 8.9 | 9.3 | 84 | 73 | 82 | 7 | >99 |
| 7 | 86.3 | 2.8 | 1.7 | La | 9.2 | 3.1 | 96 | 66 | 76 | 15 | >99 |
| 8 | 94.3 | 2.9 | 1.8 | Fe* | 1.0 | 4.0 | 94 | 38 | 60 | 30 | >99 |
| 9 | 85.4 | 2.7 | 1.7 | Th | 10.2 | 3.1 | 95 | 71 | 80 | 13 | 97 |
| 10 | 84.2 | 8.6 | 2.7 | La | 3.0 | 9.2 | 86 | 67 | 76 | 18 | >99 |
| | | | | Ce | 1.5 | | | | | | |
| 11 | 91.3 | 2.8 | — | Cs | 5.9 | 3.0 | 72 | 56 | 71 | 16 | 99 |
| 12 | 67.5 | 13.3 | — | Ta | 19.2 | 16.5 | 76 | 25 | 51 | 14 | 99 |

*Additional Deacon Catalyst
**Based on total cation content of the Deacon Catalyst and metal salt carrier, excluding promoters.

As discussed in Example 3, the HF and $CO_2/CH_4$ values herein indicate that efficient oxychlorofluorination is taking place.

| | | |
|---|---|---|
| HF Conversion | — | 36 % |
| HCl Utilization | — | 28 % |
| $Cl_2$ Utilization | — | 52 % |

Gas chromatographic analysis of the same organic effluent showed the following results:

| Component | Wt. % | Component | Wt. % |
|---|---|---|---|
| $CH_4$ | 12.6 | $CHCl_2F$ | 0.2 |
| $CO_2$ | 0.3 | $CFCl_3$* | 56.8 |
| $CH_3Cl$ | 11.1 | $CHCl_3$ | 1.0 |
| $CF_2Cl_2$ | 4.7 | $CCl_4$ | 13.4 |

*Some $CH_2Cl_2$ present with the $CFCl_3$.

The above results show that an efficient oxychlorofluorination reaction took place.

EXAMPLE 15

A 616 g sample of ⅛ inch diameter MgO pellets was treated with HF at 40 g/h for 8 hours and then at 50 g/h for 7 hours. A slight $N_2$ dilution was maintained. The temperature was gradually increased from 25° to 506° during the heating period. Based on the weight gain the fluorinated MgO had a 75% $MgF_2$ content.

A 400 ml (617.5g) sample of fluorinated MgO was impregnated with 2.0% $CuCl_2$ and 1.1% KCl to give a catalyst having a metal composition of 96.7% Mg, 2.1% Cu and 1.2% K (Deacon catalyst cation concentration -2.1%).

A gaseous mixture of $CH_4/Cl_2/HF/O_2/HF/O_2/CCl_4$ having a mole ratio of 1.0/1.25/1.50/1.38/1.50 was passed through a bed of the catalyst at 450° C. The contact time was 10 seconds.

Wet analysis of the effluent, after removal of the acidic components by condensation and phase separation, showed the following results:

| | | |
|---|---|---|
| HF Conversion | — | 92 % |
| HCl Utilization | — | 30 % |
| $Cl_2$ Utilization | — | 52 % |

Gas chromatographic analysis of the same organic effluent showed the major products to be $CH_3Cl$, $CH_2Cl_2$, $CHCl_3$, $CCl_4$, $CFCl_3$, $CF_2Cl_2$, $CHFCl_2$ and $CHF_2Cl$. The above data demonstrate that an efficient oxychlorofluorination reaction took place.

EXAMPLES 16 – 19

The effect of using a recycle versus no recycle in an oxychlorofluorination reaction is reported in these Examples:

The catalyst in all of these Examples, consisted of an alpha form of $AlF_3$ as carrier, which was impregnated with $CuCl_2$ and KCl to give a metal composition of 80.5% Al, 14.6% Cu and 4.9% K (Deacon catalyst cation concentration - 15.35%). A 450 ml. charge of catalyst pellets ( inch diameter) was employed.

Example 16 shows the results of an experiment in which no recycle was used. The flow rates were based on the following equation:

$$CH_4 + Cl_2 + 2 HF + 3/2 O_2 \rightarrow CF_2Cl_2 + 3 H_2O.$$

In Examples 17-19, a recycle consisting of $CFCl_3$ or an equimolar mixture of $CCl_4$ and $CFCl_3$ was used. The flow rates in these Examples were based on the following equation:

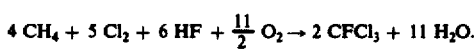

$$4 CH_4 + 5 Cl_2 + 6 HF + \frac{11}{2} O_2 \rightarrow 2 CFCl_3 + 11 H_2O.$$

The amount of recycle was equal to 1.5 moles of recycle per mole of $CH_4$ charged. The other conditions employed and the results are tabulated in Table II.

TABLE II

| Example | 16 | 17 | 18 | 19 |
|---|---|---|---|---|
| Recycle | None | $CCl_4$ | $CCl_4/CFCl_3$ | $CFCl_3$ |
| Reactor Temp. | 390° | 400° | 400° | 400° |
| Contact Time (Sec.) | 10 | 10 | 10 | 10 |
| Flow m/h | | | | |
| $CH_4$ | .54 | .44 | .44 | .44 |
| $Cl_2$ | .54 | .55 | .55 | .55 |
| HF | 1.06 | .68 | .70 | .71 |
| $O_2$ | .81 | .61 | .61 | .61 |
| Recycle | None | .76 | .62 | .59 |
| % HF Conversion | 27 | 93 | 61 | 50 |
| % $Cl_2$ Utilization | 93 | 70 | 82 | 87 |
| % HCl Utilization | 89 | 55 | 72 | 79 |
| % $CO_2/CH_4$ | 20 | 22 | 16 | 17 |
| Moles $CF_2Cl_2$ formed* | .043 | .11 | .17 | .56 |
| Moles $CH_4$ converted to halocarbons | | | | |

*Basis used to compare relative amounts of $CF_2Cl_2$ formed.

EXAMPLES 20-21

Examples 20-21 show the comparative results of oxychlorofluorination reactions on methane with a catalyst composition attempted to be prepared according to British Patent 745,818 versus a typical catalyst composition according to this invention. The results are averages of a statistically designed set of experiments which use the average values of eight experiments for each catalyst. The parameters for the oxychlorofluorination reaction were as follows:

| | |
|---|---|
| Charge (Vol.) of Catalyst | 110 ml (10/20 mesh) |
| Reaction Temperature | 440°, 460° |
| Contact Time (seconds) | 3, 5 |
| Mole Ratios $HCl/CH_4+CH_2Cl_2$ | 1.25, 1.86 |
| $HF/CH_4+CH_2Cl_2$ | 1.5, 2.0 |
| $O_2/CH_4+CH_2Cl_2$ | 1.0, 1.38 |
| Recycle $CFCl_3/CCl_4$ | 50/50, 80/20 |
| Recycle Ratio $CFCl_3—CCl_4/CH_4—CH_2Cl_2$ | 2/1, 4/1 |

Preparation of Catalyst of British Patent 745,818

A sample of $Al_2(SiF_6)_3$ was mixed with 9% NaCl and pellets of abpout ¼ inch diameter were formed. The pellets were then heated to 950° to drive off $SiF_4$ gas.

It was attempted to impregnate the resulting $AlF_3$ pellets with 31% $CuCl_2$ loading as prescribed in the British Patent. This corresponds to 45.7% Al, 38.6% Cu and 15.7% Na or a Deacon cation concentration of 45.8%. It was only possible to achieve a 23% $CuCl_2$ loading corresponding to 52.2% Al, 30.0% Cu and 17.8% Na and a Deacon catalyst cation concentration of 36.4%.

Preparation of the Comparison Catalyst

The comparison catalyst was prepared by the high temperature fluorination of a commercial alumina (Harshaw Al-0104) followed by impregnation with $CuCl_2/KCl$ as described in EXAMPLE 2 herein.

The reactions of both Examples were performed in an alumina lined one inch tubular reactor. Catalyst bed height was 14 inches,. During the reaction with the British patent catalyst, there was considerable run-off of the $CuCl_2$. This decreased the $CuCl_2$ content to 14.1% corresponding to 60.6% Al, 18.8% Cu and 20.6% Na and a Deacon catalyst cation concentration of 23.6%. The run-off of $CuCl_2$ caused considerable operating problems due to plugging, indue vaporization, excessive corrosion and lower activity due to deactivation of the fluorination sites on the carrier. Furthermore, the British patent catalyst was not fluidizable. The results of the comparative tests are shown in the following Table:

TABLE III

| Example | 20 | 21 |
|---|---|---|
| Catalyst | British Patent | Comparison Catalyst of the Invention |
| Deacon Catalyst Cation Concentration | 36.4% (at beginning of reaction) 23.6% (during the reaction) | 2.8% |
| % $CH_4$ Yield | 75.1 | 87.0 |
| % $O_2$ Yield | 57.2 | 81.6 |
| % HF Conversion | 48.7 | 72.8 |
| % HCl Utilization | 40.4 | 55.7 |
| lbs $CF_2Cl_2$ produced/hr/$ft^3$ Catalyst | 3.33 | 7.40 |
| Corrosion (Inches/year-Inconel Test Coupon) | >0.4 | <0.4 |
| Properties | High Copper Loss Non-Fluidizable | Low Copper Loss Fluidizable |

The above data demonstrate the relative ineffectiveness of the British patent catalyst for oxychlorofluorination purposes.

EXAMPLES 22-23

These Examples demonstrate the oxychlorofluorination of methane with a fluidized catalyst bed. The reactor was a ceramic lined pipe, 4 inches in diameter and 20 feet long. A sintered Inconel perforated disc at the bottom of the reactor served to support the fluid bed and distribute the incoming gaseous reactants.

The catalyst used in these Examples was a commercial powdered $AlF_3$ which was impregnated with $CuCl_2$/KCl to give a composition of 91.3% Al, 5.7% Cu and 3.0% K (Deacon catalyst cation concentration - 5.8%). A sieve analysis of the coated catalyst showed the mean particle size to be 81.8 microns.

The following Table shows the results obtained under the conditions described:

TABLE IV

| Example | 22 | 23 |
|---|---|---|
| Catalyst Charge (liters) | 12 | 15 |
| Bed Height (ft) | 8 | 10 |
| Temperature (° C) | 460 | 460 |
| Pressure (psig.) | 20 | 20 |
| Contact Time (seconds) | 8.5 | 10.8 |
| Gas Velocity (ft/sec) | 0.95 | 0.92 |
| Feed (m/h) | | |
| HF | 40.8 | 43.2 |
| HCl | 34.6 | 39.4 |
| $O_2$ | 37.3 | 33.1 |
| $CFCl_3$ | 70.8 | 0 |
| $CH_2Cl_2$ | 17.8 | 11.9 |
| $CH_4$ | 10.1 | 11.0 |
| $N_2$ | 0 | 69.0 |
| Product Composition (m/h) | | |
| $O_2$ | 8.80 | 5.77 |
| CO | 0 | 0 |
| $CH_4$ | 1.26 | 0 |
| $CO_2$ | 8.92 | 5.40 |
| $CHF_3$ | .02 | 0 |
| $CF_2Cl_2$ | 8.22 | 2.05 |
| $CH_3Cl$ | .15 | 0 |
| $CH_2FCl$ | .29 | 0 |
| $CFCl_3$ | 73.0 | 8.71 |
| $CH_2Cl_2$ | .56 | .17 |
| $CHCl_3$ | 3.26 | 3.01 |
| $CCl_4$ | 2.78 | 2.25 |
| HCl | 21.65 | 14.25 |
| HF | 23.77 | 28.75 |
| $H_2O$ | 43.69 | 45.62 |
| $N_2$ | 0 | 69.0 |
| | Conversion (%) | Utilization (%) | Conversion (%) | Utilization (%) |
| HCl | 37.4 | 58.1 | 63.9 | 73.5 |
| HF | 41.9 | 99.7 | 33.4 | 100.0 |
| $O_2$ | 76.4 | 68.7 | 82.6 | 80.3 |
| Carbon Feed ($CH_4$+ $CH_2Cl_2$) | 95.5 | 66.4 | 100.0 | 76.5 |

The above data demonstrate the efficient oxychlorofluorination reactions achieved in the fluidized bed reactors.

EXAMPLE 24

A 180 ml. sample (3/16 inch pellets) of a $AlF_3$ catalyst which consisted of a mixture of 40% of the alpha form and 60% of the gamma form was coated with $CuCl_2$/KCl to give metal composition which was 97.7% Al, 1.5% Cu and 0.8% K (Deacon catalyst cation concentration -1.5%). The catalyst was charged to a 1 × 20 inches Inconel tubular reactor and an oxychlorofluorination reaction was conducted as generally described in EXAMPLE 3 under the conditions described below:

Reaction Temperature was 434°
Contact Time was 4.9 seconds.

| Reactant Feed (m/h) | | |
|---|---|---|
| HF | — | 0.524 |
| HCl | — | .427 |
| $O_2$ | — | .498 |
| $CCl_4$ | — | .253 |
| $CFCl_3$ | — | .240 |
| $CH_2Cl_2$ | — | .210 |
| $CH_4$ | — | .121 |

The results are shown below:

| Product Composition (m/h) | | | | |
|---|---|---|---|---|
| $O_2$ | — | 0.223 | $CHFCl_2$ | — | .024 |
| CO | — | .002 | $CFCl_3$ | — | .401 |
| $CH_4$ | — | .013 | $CH_2Cl_2$ | — | .020 |
| $CO_2$ | — | .046 | $CHCl_3$ | — | .084 |
| $CF_3Cl$ | — | .005 | $CCl_4$ | — | .104 |
| $CHF_2Cl$ | — | .010 | HCl | — | .455 |
| $CF_2Cl_2$ | — | .077 | HF | — | .155 |
| $CHF_2Cl$ | — | .010 | $Cl_2$ | — | .002 |
| $CH_3Cl$ | — | .005 | $H_2O$ | — | .472 |

| | Conversion (%) | Utilization (%) |
|---|---|---|
| $CH_4$ | 89.0 | 47.3 |
| HCl | — | 42.7 |
| HF | 70.4 | 96.2 |
| $O_2$ | 55.2 | 82.2 |

The above data show that an efficient oxychlorofluorination reaction took place.

EXAMPLE 25

A 20 ml. sample (10-20 mesh size) of alpha $AlF_3$ was coated with $CuCl_2$/KCl to give a metal composition of 87.7% Al, 7.7% Cu and 4.6% K (Deacon catalyst cation concentration -8.7%). This composition was charged to a 1 × 20 inches tubular Inconel reactor and an oxychlorofluorination experiment was performed as generally described in Example 3, but under the conditions described below.

Reactor Temperature was 419°.
Contact Time was 1.7 seconds.

| Reactant Feed (m/h) | | |
|---|---|---|
| HF | — | 0.175 |
| $O_2$ | — | .159 |
| $CCl_4$ | — | .087 |
| $CFCl_3$ | — | .087 |
| $CH_4$ | — | .116 |

The results were as follows:

| Product Composition (m/h) | | | | | |
|---|---|---|---|---|---|
| $O_2$ | — | 0.349 | $CHFCl_2$ | — | .002 |
| CO | — | .003 | $CFCl_3$ | — | .168 |
| $CH_4$ | — | .016 | $CH_2Cl_2$ | — | .014 |
| $CO_2$ | — | .014 | $CHCl_3$ | — | .023 |
| $CF_3Cl$ | — | .000 | $CCl_4$ | — | .047 |
| $CHF_2Cl$ | — | .000 | HCl | — | .130 |
| $CF_2Cl_2$ | — | .006 | HF | — | .031 |
| $CHF_2Cl$ | — | .000 | $Cl_2$ | — | .000 |
| $CH_3Cl$ | — | .008 | $H_2O$ | — | .180 |

| | Conversion (%) | Utilization (%) |
|---|---|---|
| $CH_4$ | 86.0 | 83.9 |
| HCl | 100.0 | 70.1 |
| HF | 82.3 | 100.0 |
| $O_2$ | 78.1 | 88.2 |

The above data demonstrate that an efficient oxychlorofluorination reaction was carried out.

EXAMPLES 26-39

Oxychlorofluorination reactions are conducted as described in EXAMPLE 3, except with conditions, starting materials and catalyst compositions changed as described in the following Table:

TABLE V

| Example | Starting Material | Deacon Catalyst | Support | Promoter | Temperature | Pressure | Deacon Catalyst | Contact Time (second) |
|---|---|---|---|---|---|---|---|---|
| 26 | ethane | $Cu_2O$ | $MgF_2$ | LiCl | 425 | 14.7 | 4 | 9 |
| 27 | ethylene | $FeCl_2$ | $CaF_2$ | NaCl | 300 | 14.7 | 0.6 | 20 |
| 28 | propane | $Cr_2O_3$ | $BaF_2$ | RbCl | 600 | 200 | 20 | .1 |
| 29 | propylene | $MnBr_2$ | $V_2O_3$ | $LaCl_3$ | 550 | 20 | 1 | 18 |
| 30 | butane | $SnCl_2$ | $ThF_4$ | $TaCl_5$ | 350 | 75 | 16 | 2 |
| 31 | isobutylene | $NiBr_2$ | $SrF_2$ | KCl | 500 | 50 | 2 | 6 |
| 32 | methyl chloride | $RhCl_3$ | $CoF_2$ | $TaCl_5$ | 500 | 40 | 8 | 3 |
| 33 | methyl fluoride | $VCl_3$ | $NiF_2$ | CsCl | 375 | 30 | 7.5 | 6 |
| 34 | ethylene chloride | $CoO_2$ | $CdF_2$ | — | 450 | 25 | 19 | 12 |
| 35 | ethylene difluoride | $PdCl_2$ | PbO | — | 475 | 14.7 | 0.8 | 18 |
| 36 | vinyl chloride | $Cd(NO_3)_2$ | $CrF_3$ | — | 325 | 14.7 | 1.5 | 15 |
| 37 | 1,1-dichlorobutane | $HgBr_2$ | $Fe_2O_3$ | — | 625 | 225 | 2.5 | 10 |
| 38 | ethyl chloride | $PbCl_2$ | $AlF_3$ | — | 575 | 250 | 5 | 4 |
| 39 | 1-chlorobutadiene | $Ce(NO_3)_3$ | $AlF_3$ | — | 550 | 350 | 1.12 | 5 |

The oxychlorofluorination reactions proceed in a satisfactory manner in all of Examples 26-39.

We claim:

1. The process for the production of chlorofluorinated acyclic hydrocarbons which comprises reacting a gaseous mixture of a starting material selected from an acyclic hydrocarbon containing up to four carbon atoms and an acyclic hydrohalocarbon containing up to four carbon atoms in which the halo atoms are selected from chloro and fluoro, or mixtures thereof, at least 0.25 mole oxygen in an oxygen-containing gas for each C-H bond in the starting material, at least 0.50 mole HCl or equivalent amount of $Cl_2$ for each C-H bond and C=C bond present in the starting material, and HF, in the presence of a Deacon catalyst supported by a stable, inert metal salt carrier, with the weight percentage of cation in the Deacon catalyst ranging from about 0.6-20 based on the total cation content of the Deacon catalyst and metal salt carrier, at elevated temperatures and with a contact time of from about 0.1-20 seconds.

2. The process according to claim 1 in which the starting material is an acyclic hydrocarbon.

3. The process according to claim 1 in which the catalyst bed is maintained as a fixed bed and in which the contact time is from about 0.1-18 seconds.

4. The process according to claim 3 in which the contact time is from about 2-5 seconds.

5. The process according to claim 1 in which the catalyst bed is maintained as a dynamic bed.

6. The process according to claim 5 in which the catalyst bed is maintained as a fluidized bed and in which the contact time is from about 3-20 seconds.

7. The process according to claim 6 in which the contact time is from about 6-12 seconds.

8. The process according to claim 1 in which the elevated temperatures range from about 250-600° C.

9. The process according to claim 1 in which at least 0.50 mole oxygen in an oxygen-containing gas per C-H bond in the starting material is employed.

10. The process according to claim 1 in which at least 0.75 mole HCl or equivalent amount of $Cl_2$ for each C-H bond and C=C bond present in the starting material is employed.

11. The process according to claim 1 in which at least 1 mole HCl or equivalent amount of $Cl_2$ for each C-H bond and C=C bond present in the starting material is employed.

12. The process according to claim 1 in which the Deacon catalyst is a metal halide.

13. The process according to claim 12 in which the Deacon catalyst is promoted with a metal salt in which the metal is selected from the group consisting of Li, Na, K, Rb, La and Cs.

14. The process according to claim 1 in which the Deacon catalyst is a copper halide.

15. The process according to claim 1 in which the Deacon catalyst is $CuCl_2$.

16. The process according to claim 1 in which the carrier is a metal salt in which the metal is selected from the group consisting of Al, Mg, Ca, Ba, V, Th, Sr, Co, Ni, Cd, Pb, Cr and Fe, or combinations thereof.

17. The process according to claim 16 in which the anion of the salt is a fluoride.

18. The process according to claim 17 in which the metal salt is $AlF_3$.

19. The process according to claim 18 in which the AlF$_3$ is substantially in alpha form.

20. The process according to claim 2 in which at least .50 mole oxygen in an oxygen-containing gas per C-H bond in the starting material is employed.

21. The process according to claim 2 in which at least .75 mole HCl or equivalent amount of Cl$_2$ for each C-H bond and C=C bond present in the starting material is employed.

22. The process according to claim 2 in which the aliphatic hydrocarbon is methane.

23. The process according to claim 2 in which the aliphatic hydrocarbon is unsaturated and contains from 2-4 carbon atoms.

24. The process according to claim 2 in which the aliphatic hydrocarbon is saturated and contains from 2-4 carbon atoms.

25. The process according to claim 2 in which the aliphatic hydrocarbon is ethane.

26. The process according to claim 2 in which the aliphatic hydrocarbon is ethylene.

27. The process according to claim 2 in which the aliphatic hydrocarbon is propane.

28. The process according to claim 2 in which the aliphatic hydrocarbon is propylene.

29. The process according to claim 2 in which the aliphatic hydrocarbon is butane.

30. The process according to claim 2 in which the aliphatic hydrocarbon is isobutylene.

31. The process according to claim 2 in which the contact time is from about 2-12 seconds.

32. The process according to claim 1 in which the starting material containing a gaseous mixture is diluted with an inert gas.

33. The process according to claim 1 in which one or more halogenated hydrocarbons from the product mixture are recycled to the reaction mixture.

34. The process according to claim 2 in which the weight percentage of cation in the Deacon catalyst ranges from about 1-16 based on the total cation content of the Deacon catalyst and metal salt carrier.

35. The process according to claim 2 in which the catalyst bed is maintained as a dynamic bed.

36. The process according to claim 34 in which the catalyst bed is maintained as a fluidized bed.

37. The process according to claim 34 in which the elevated temperatures range from about 250°-600° C.

38. The process according to claim 34 in which the Deacon catalyst is a metal halide.

39. The process according to claim 38 in which the Deacon catalyst is promoted with a metal salt in which the metal is selected from the group consisting of Li, Na, K, Rb, La and Cs.

40. The process according to claim 34 in which the Deacon catalyst is a copper halide.

41. The process according to claim 34 in which the Deacon catalyst is CuCl$_2$.

42. The process according to claim 34 in which the carrier is a metal salt in which the metal is selected from the group consisting of Al, Mg, Ca, Ba, V, Th, Sr, Co, Ni, Cd, Pb, Cr and Fe.

43. The process according to claim 42 in which the anion of the salt is a fluoride.

44. The process according to claim 43 in which the metal salt is AlF$_3$.

45. The process according to claim 34 in which the aliphatic hydrocarbon is unsaturated and contains from 2-4 carbon atoms.

46. The process according to claim 34 in which the aliphatic hydrocarbon is saturated and contains from 2-4 carbon atoms.

47. The process according to claim 36 in which the aliphatic hydrocarbon is methane.

48. The process according to claim 34 in which one or more halogenated hydrocarbons from the product mixture are recycled to the reaction mixture.

49. The process according to claim 34 in which the reaction gas mixture is diluted with an inert gas.

50. The process according to claim 34 in which the weight percent of cation in the Deacon catalyst range from about 2-8 based on the total cation content of the Deacon catalyst and metal salt.

51. The process according to claim 34 in which the Deacon catalyst is a metal halide and in which the carrier is a metal salt in which the metal is selected from the group consisting of Al, Mg, Ca, Ba, Th, Sr, Co, Ni, Cd, Pb, Cr and Fe.

52. The process according to claim 51 in which the Deacon catalyst is CuCl$_2$.

53. The process according to claim 51 in which the anion of the metal salt carrier is a fluoride.

54. The process according to claim 53 in which the metal salt is aluminum fluoride.

55. The process according to claim 52 in which the metal salt carrier is AlF$_3$.

56. The process according to claim 54 in which the AlF$_3$ is substantially in the alpha form.

57. The process according to claim 51 in which the aliphatic hydrocarbon is saturated.

58. The process according to claim 57 in which the aliphatic hydrocarbon is methane.

59. The process according to claim 53 in which one or more halogenated hydrocarbons from the product mixture are recycled to the reaction mixture.

60. The process according to claim 59 in which the aliphatic hydrocarbon is saturated.

61. The process according to claim 53 in which the starting material containing gas mixture is diluted with an inert gas.

62. The process according to claim 61 in which the Deacon catalyst is promoted with a metal salt in which the metal is selected from the group consisting of Li, Na, K, Rb, La and Cs.

63. The process according to claim 62 in which the aliphatic hydrocarbon is methane.

64. The process according to claim 63 in which the elevated temperatures range from about 250°-600° C.

65. The process according to claim 63 in which the weight percentage of cation in the Deacon catalyst ranges from about 2-8 based on the total cation content of the Deacon catalyst and metal salt.

66. The process according to claim 64 in which the Deacon catalyst is CuCl$_2$.

67. The process according to claim 66 in which the metal salt support is aluminum fluoride.

68. The process according to claim 67 in which the aluminum fluoride is substantially in the alpha form.

69. The process according to claim 68 in which the contact time is about 2-12 seconds.

70. The process for the production of chlorofluorinated acyclic hydrocarbons which comprises reacting a gaseous mixture of a starting material selected from an acyclic hydrocarbon containing up to four carbon atoms and an acyclic hydrohalocarbon containing up to four carbon atoms in which the halo atoms are selected from chloro and fluoro, or mixtures thereof, at least .25 mole oxygen in an oxygen-containing gas for each C-H bond in the starting material, at least 2 mole HCl or equivalent amount $Cl_2$ for each mole of starting material, and Hf, in the presence of a Deacon catalyst supported by a stable, inert metal salt carrier, with the weight percentage of cation in the Deacon catalyst ranging from about 0.6-20 based on the total cation content of the Deacon catalyst and metal salt carrier, at elevated temperatures and with a contact time of from about 0.1-20 seconds.

71. The process according to claim 70 in which the starting material is methane.

72. The process according to claim 71 in which the Deacon catalyst is a copper halide.

73. The process according to claim 72 in which the metal salt is $AlF_3$.

74. The process according to claim 73 in which the catalyst bed is maintained as a fluidized bed and in which the contact time is from about 6-12 seconds.

* * * * *